(12) United States Patent
Xiong et al.

(10) Patent No.: US 11,707,191 B2
(45) Date of Patent: Jul. 25, 2023

(54) CALIBRATION AND IMAGE PROCESSION METHODS AND SYSTEMS FOR OBTAINING ACCURATE PUPILLARY DISTANCE MEASUREMENTS

(71) Applicant: EyeQue Inc., Newark, CA (US)

(72) Inventors: Yuan Xiong, Newark, CA (US); John Serri, Newark, CA (US); Noam Sapiens, Newark, CA (US)

(73) Assignee: EyeQue Inc., Newark, CA (US)

( * ) Notice: Subject to any disclaimer, the term of this patent is extended or adjusted under 35 U.S.C. 154(b) by 685 days.

(21) Appl. No.: 16/593,626

(22) Filed: Oct. 4, 2019

(65) Prior Publication Data
US 2020/0107720 A1    Apr. 9, 2020

Related U.S. Application Data

(60) Provisional application No. 62/741,745, filed on Oct. 5, 2018.

(51) Int. Cl.
*A61B 3/11* (2006.01)
*A61B 5/107* (2006.01)
(Continued)

(52) U.S. Cl.
CPC ............ *A61B 3/111* (2013.01); *A61B 3/0025* (2013.01); *A61B 3/107* (2013.01); *A61B 5/0077* (2013.01);
(Continued)

(58) Field of Classification Search
CPC ......... A61B 3/10; A61B 3/1005; A61B 3/107; A61B 3/11; A61B 3/111; A61B 3/0016;
(Continued)

(56) References Cited

U.S. PATENT DOCUMENTS

| 4,845,641 A * | 7/1989 | Ninomiya | ............ | G02C 13/003 |
| | | | | 348/121 |
| 2007/0195266 A1* | 8/2007 | Kubitza | ............... | G02C 13/005 |
| | | | | 351/204 |

(Continued)

OTHER PUBLICATIONS

Murray, et al. "The reliability, validity, and normative data of interpupillary distance and pupil diameter using eye-tracking technology." Translational vision science & technology 6.4 (2017): 2-2. (Year: 2017).*

*Primary Examiner* — David J. McCrosky
(74) *Attorney, Agent, or Firm* — Steven A. Nielsen; www.NielsenPatents.com

(57) ABSTRACT

Accurate measurement of pupillary distance, PD, is necessary to make prescription eye glasses as well as configuring VR headsets, and using other binocular optical devices. Today, many people are ordering eyeglasses on line and obtaining their PD is often problematic for a number of reasons as the prior art fails to provide consumer friendly PD measurement systems. A disclosed eyeglass frame system comprises reference marks of known locations upon the frames. A smart phone may be used to locate the consumer's pupils, while the consumer is wearing the frames. The consumer's pupils may be marked or tagged upon a digital image of the consumer wearing the frames. By use of angles in the sight lines of the camera lens and other variable values and the known relative distances of the frame markings, a consumer's pupillary distance can be quickly and accurately derived.

15 Claims, 17 Drawing Sheets

(51) Int. Cl.
    *A61B 5/00*         (2006.01)
    *A61B 3/107*       (2006.01)
    *A61B 3/00*         (2006.01)
    *A61B 90/00*       (2016.01)
    *A61B 90/50*       (2016.01)

(52) U.S. Cl.
    CPC .......... *A61B 5/1071* (2013.01); *A61B 5/1079* (2013.01); *A61B 5/6898* (2013.01); *A61B 5/7225* (2013.01); *A61B 5/7278* (2013.01); *A61B 2090/3937* (2016.02); *A61B 2090/502* (2016.02); *A61B 2576/02* (2013.01)

(58) Field of Classification Search
    CPC ... A61B 3/0025; A61B 3/0033; A61B 3/0066; A61B 3/0083; A61B 5/0077; A61B 5/1071; A61B 5/1079; A61B 5/6898; A61B 5/7225; A61B 5/7278; A61B 2090/3937; A61B 2090/502; A61B 2576/02; A61B 3/024; A61B 3/103; A61B 5/1072; G02C 13/003; G02C 13/005
    See application file for complete search history.

(56) References Cited

U.S. PATENT DOCUMENTS

2016/0327814 A1\* 11/2016 Marie ..................... G06T 7/001
2016/0327815 A1\* 11/2016 Rego ................... G02C 13/003
2016/0357032 A1\* 12/2016 Cabeza-Guillen ... G02C 13/005

\* cited by examiner

View Angle and Focal Length

CALIBRATION AND IMAGE PROCESSION METHODS AND SYSTEMS FOR OBTAINING ACCURATE PUPILLARY DISTANCE MEASUREMENTS

CROSS-REFERENCE TO RELATED APPLICATIONS

This application claims the benefit of and priority date of provisional patent application 62/741,745 filed on Oct. 5, 2018, the contents of which are incorporated herein.

This application includes material which is subject or may be subject to copyright and/or trademark protection. The copyright and trademark owner(s) has no objection to the facsimile reproduction by any of the patent disclosure, as it appears in the Patent and Trademark Office files or records, but otherwise reserves all copyright and trademark rights whatsoever.

BACKGROUND OF THE INVENTION

(1) Field of the Invention

The invention generally relates to measuring pupillary distance or PD. More particularly, the invention relates to means and methods of calibration and image processing to obtain a PD value.

(2) Description of the Related Art

The known related art fails to anticipate or disclose the principles of the present invention.

In the related art, PD rulers may include linear rulers with longitudinal voids for each eye and a nose void. A user places the ruler upon their nose and looks through the voids, with each void having measurement indicia at the perimeter. The user then attempts to look into a mirror and see where the measurement markings align with their pupils. As the user's eyes dart back and forth, looking for measurement markings aligning to a pupil, no accurate measurement may be obtained with the pupil a straight forward position. Moreover, self-administered PD ruler measurements fail to distinguish between near and far PD measurements.

A helper may be involved in observing a user's pupils through the voids, but a helper's observations are often compromised with parallax problems. Using a ruler, a skilled optician may be able to obtain a PD measurement to accuracy of about 1 mm.

In the prior art, optician PD alignment tools are typically cost prohibitive for consumer use and require a degree of skill.

In the prior art, auto refractors may measure and report PD values, but our prohibitively expensive and are far from being portable.

In the prior art, PD measurement apps that operate upon desktop or laptop computers and/or smartphones are known, but are fraught with shortfalls. Such apps may need an absolute reference in order to work correctly and prone to calculational and alignment errors. What is often used for a reference is to place a credit card under the nose or forehead and to take a picture of the person. The credit card serves as the reference, but is subject to various parallax errors that can cause PD calculation errors that exceed 1 mm. PD apps may take two forms, manual and auto wherein both forms are prone to problems related to obtaining or even recognizing near PD vs. far PD. The apps of the prior art fail to account for vergence, an issue that affects PD observation and measurement. When a person is looking at something close up their eyes are converging upon the object being viewed, thus bringing the pupils closer together. Thus the near PD is different than far PD, that is the PD when the eye is looking away at infinity. Even worse, in some phones the camera is not on the center axis and this leads to parallax errors that are normally not accounted for and can readily create errors greater than 1 mm.

The prior art is so replete with problems, that many optometrists are reluctant to give the PD to their patient, and is generally not considered part of an eye examination, even if a patient asks for their PD value they are usually directed to go to an eyeglass store to get a measurement or they are charged an extra fee by the eye doctor. Some states in the US, but not, all mandate that if the patient ask their eye doctor they are mandated to provide the PD values.

With the growing use of online eyeglass ordering, consumers are in more need than ever for fast, economical and accurate means and methods of obtaining their PD measurement. Thus, there is an urgent need in the art for the presently disclosed embodiments.

BRIEF SUMMARY OF THE INVENTION

Background of PD

One measurement of PD is the distance between the center of the right and left eye pupils. The average PD in women is about 62 mm and in men about 64 mm when the eyes are looking at an object far away. When the eyes are looking at an object up close the PD is smaller due to convergence, as the eyes focus upon a nearby object.

The Utility of PD

1. Needed for eyeglasses a) PD value is needed for making prescription eyeglasses and is used to determine the placement of the optical center of the prescription lens. The optical center needs to align with the pupil to obtain the full benefit of the lens prescription and to avoid headaches and vision problems.

b) Prescription eyeglasses made for a person presenting an inaccurate PD will cause a significant difference between the pupil of the eye and the optical center of the lens, resulting in discomfort and eye strain.

2. Virtual Reality headsets and other binocular optical interfaces need a user's true PD measurement to be effective and to avoid headaches, eye strain and visual distortion.

There are a number of PD measurement used for fitting prescription eyeglasses:

1. Distance PD is the measure PD when the eyes are staring straight ahead looking at an object far away, with such a distance including infinity.

2. Near PD is the measured PD when the eyes are focused upon a nearby object. Near PD is needed for reading glasses or progressive lenses.

3. Dual PD may comprise two measurements, the Right PD is the distance from the bridge of the nose to the center of the right eye pupil, and there is the corresponding measurement for left PD. These dual measurements are important if the Right and Left PD differ by more than 1 mm.

Disclosed embodiments overcome shortfalls in the related art by providing economic and efficient means and methods of self-administered PD measurement to within a margin of error of 1 mm or less.

Disclosed embodiments may include methods and/or means of obtaining and or performing an auto PD measurement using a personal electronic device, such as a smart phone and/or eyeglass frames comprising calibration marks or calibration indicia. The disclosed embodiments overcome the shortfalls in the prior art by, inter alia, providing an easy to use reference and by artfully managing a plethora of alignment challenges occurring between a user and a camera.

A helpful tool, disclosed herein, is the use of eyeglass frames or calibration frames with calibration marks (Ts} as shown in FIG. 1 as the references. Since the absolute spacing amongst the marks is known and the marks are near the target object of interest, the center of the eye i.e. pupils the eyeglass frame serves as an excellent absolute reference. With three or so marks upon an eyeglass frame, the disclosed embodiments may create an absolute frame position with respect to the camera of the phone.

These and other objects and advantages will be made apparent when considering the following detailed specification when taken in conjunction with the drawings.

REFERENCE NUMERALS IN THE DRAWINGS

Figure 1:
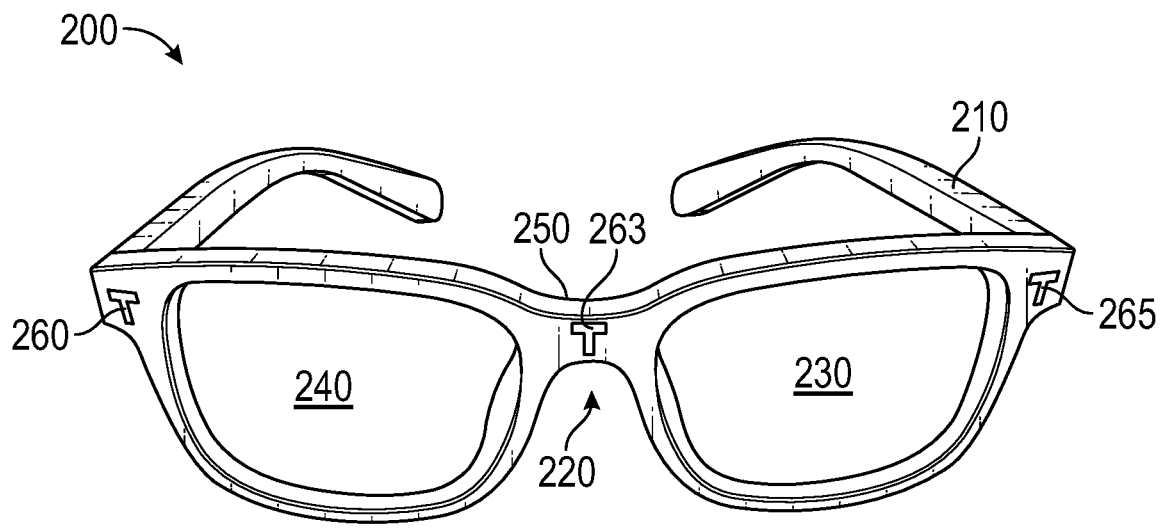
FIG. 1 reference eyeglass frames or calibration frames
FIG. 2 capture of user's face with a personal electronic device, frames on face to be added
FIG. 3 calibration frames on face with auto image detection engaged
FIG. 4 calibration frames on face using manual controls to align reference Ts
FIG. 5 calibration frames on face using manual controls to align markers with center of pupils
FIG. 6 output interface showing accurate measurements of single, dual and near PD
FIG. 7 camera space and ray structure
FIG. 8 view angle and focal length structure
FIG. 9 virtual image plane
FIG. 10 field of view configuration
FIG. 11 location of a target object beyond the imaging plane
FIG. 12 calibration frames with angles shown between T calibration points
FIG. 13 front view of calibration frames
FIG. 14 top view of calibration frames
FIG. 15 side view of calibration frames
FIG. 16 calibration frame edges as detected using Canny Edge Detection
FIG. 17 frame edge and pupil detection
FIG. 18 pixel coordinates of the "T" markers used to calculate real world coordinates
FIG. 19 relation of eyes to calibration frames
FIG. 20 inaccurate PD caused by user looking at the phone
FIG. 21 correction needed for finding near PD values
FIG. 22 determining the dual PD
FIG. 23 projection locations of pupils and T marks
FIG. 24 projections locations and angles
FIG. 25 horizontal projections of PD
FIG. 26 area viewed to find the base curve of the cornea

100 a disclosed embodiment in general
200 calibration frames or eyeglass frames
210 legs of calibration frames
220 nose area of calibration frames
230 left eye frame area
240 right eye frame area
250 center point of calibration frames
260 a first "T" or "$T_1$ marking disposed on the right temple area of the calibration frames
265 a second "T:" or $T_2$," marking disposed upon the left temple area of the calibration frames
263 a third "T' or "$T_3$" marking disposed upon the center area of the calibration frames
267 plane along the three "T" markings 260, 263 and 265
270 outer surface of calibration frames 200
280 frame angle between center and end, in the range of 5 to 12 degrees with 9 degrees as the best mode
300 calibration cross hairs or marker positions to mark a center point of a pupil
320 manual controls to adjust positions of calibration cross hairs 300
400 a single distance or single far PD value
410 dual PD values
425 near PD values
500 system user or person using a disclosed system
510 center of a pupil
700 smart phone or other personal electronic device
710 check mark or other indicia of acceptance of the positions of display overlays such as pupil cross hairs 300
720 lens or a camera or smart phone
722 position of a lens 720 or optical element
730 view ray from camera lens
732 angle x or $Ø_x$ of two view rays 730 from camera lens, the angle sometimes measured at the plane of the lens 720
735 diagonal distance sometimes measured at an image
740 CCD/CMOS sensor plane of camera or smartphone
750 vertical projection line
752 angle v or $Ø_v$ of two vertical projection lines 750, the angle sometimes measured at the plane of the lens 720
755 height of vertical projection sometimes measured at an image
760 horizontal projection lines
762 angle h or $Ø_h$ of two horizontal projection lines 760, the angle sometimes measured at the plane of the lens 720
765 width of horizontal projection, sometime measured at an image
770 field of view
800 image
805 image plane
810 scene object
820 light source
825 shadow ray
r1 distance between a lens position 722 and a first marking $T_1$ or 360
r2 distance between a lens position 722 and a second marking $T_2$ or 265
r3 distance between a lens position 722 and a third marking $T_3$ or 263
d1 distance between a second marking $T_2$ and a third marking $T_3$
d2 distance between a first marking $T_1$ and a third marking $T_3$.
d3 distance between a first marking $T_1$ and a second marking $T_2$
Ø1 angle between r2 and r3
Ø2 angle between r1 and r3
Ø3 angle between r1 and r2

DETAILED DESCRIPTION OF EMBODIMENTS OF THE INVENTION

The following detailed description is directed to certain specific embodiments of the invention. However, the invention can be embodied in a multitude of different ways as defined and covered by the claims and their equivalents. In this description, reference is made to the drawings wherein like parts are designated with like numerals throughout.

Unless otherwise noted in this specification or in the claims, all of the terms used in the specification and the claims will have the meanings normally ascribed to these terms by workers in the art.

Unless the context clearly requires otherwise, throughout the description and the claims, the words "comprise," "comprising" and the like are to be construed in an inclusive sense as opposed to an exclusive or exhaustive sense; that is to say, in a sense of "including, but not limited to." Words using the singular or plural number also include the plural or singular number, respectively. Additionally, the words "herein," "above," "below," and words of similar import, when used in this application, shall refer to this application as a whole and not to any particular portions of this application.

The above detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while steps are presented in a given order, alternative embodiments may perform routines having steps in a different order. The teachings of the invention provided herein can be applied to other systems, not only the systems described herein. The various embodiments described herein can be combined to provide further embodiments. These and other changes can be made to the invention in light of the detailed description.

Any and all the above references and U.S. patents and applications are incorporated herein by reference. Aspects of the invention can be modified, if necessary, to employ the systems, functions and concepts of the various patents and applications described above to provide yet further embodiments of the invention.

Referring to FIG. 1, calibration frames 200 overcome many shortfalls in the related art as the calibration frames fit easily upon the head of a user and are stationary when worn, which is a stark contract the prior art's use of credit cards held to a user's head and the other prior art solutions.

In particular, the disclosed calibration frames overcome the short falls of credit cards and other prior art objects used as reference points, as the disclosed calibration frames:

1. Comprise calibration marks that fall naturally near the eyes.

2. Comprise a center calibration mark (T) 263 rests upon the bridge of the nose, a reference point needed for assessing dual PD.

3. After the calibration frames are put on the user, the user does not need to adjust or hold the calibration frames, leaving the user's hands available to operate a camera or personal electronic device that may employ the disclosed methods of image management and PD calculation.

The disclosed calibration frames 200 overcome shortfalls in the prior art by, inter alia, comprising frame components that are disposed in parallel to a plane that contains the pupil of the user's eyes. By knowing or ascertaining the distance between the two planes, the plane of the pupils and plane of the relevant frame components, an image or images may be formed and then the PD values may be calculated as disclosed herein.

Figure 4:
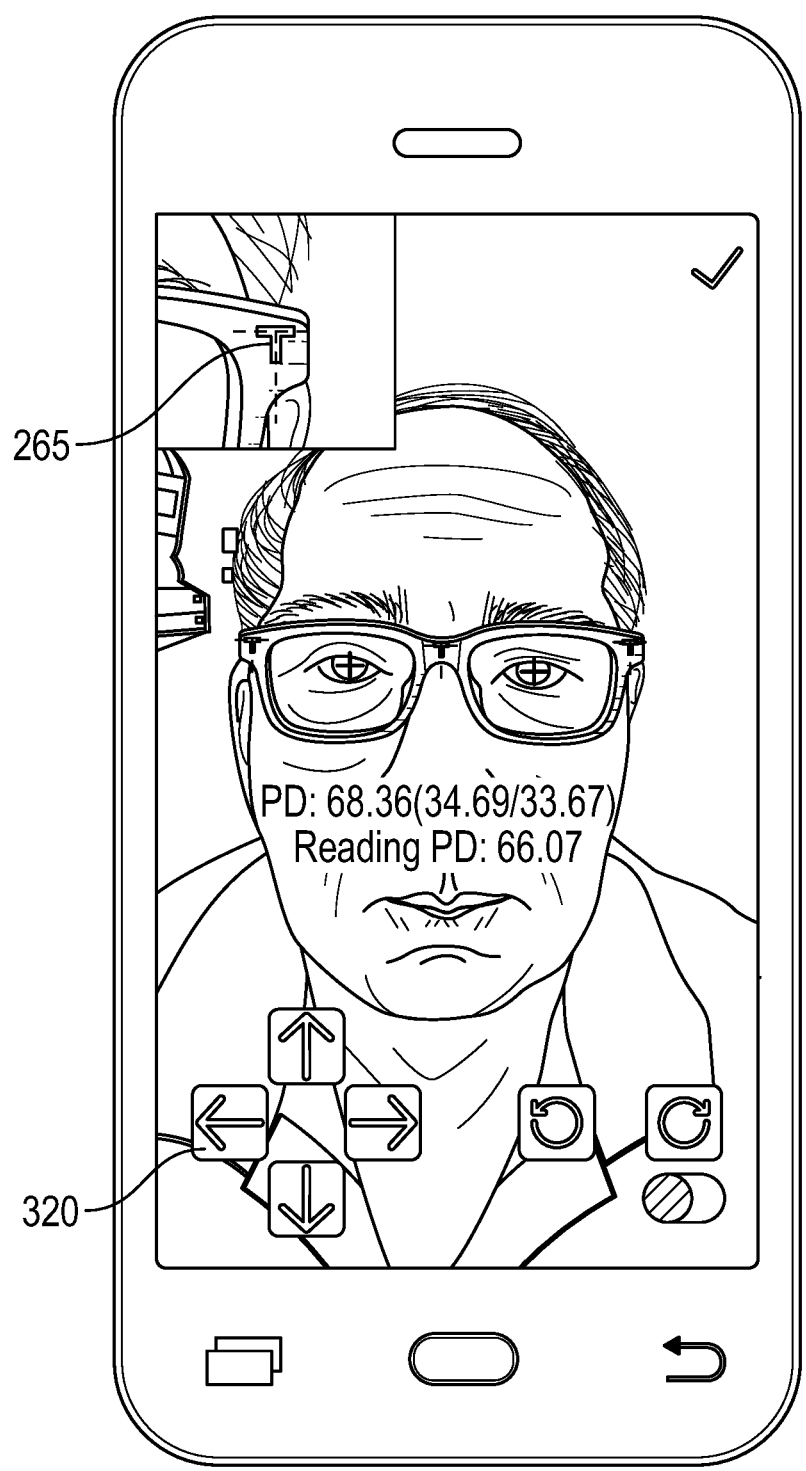

As more fully described herein, the disclosed systems and methods may first perform an auto PD measurement, using image processing to find the calibration "T" marks and then finding the center of a pupil and then marking a screen overlay with images of the "T" calibration marks and pupil centers and/or other relevant points of interest. The location of the "T" marks, pupil centers may be found automatically using the disclosed systems and interfaces, or, as shown in FIG. 4 interfaces may be provided to allow a user to manually locate relevant points of interest.

Figure 2:
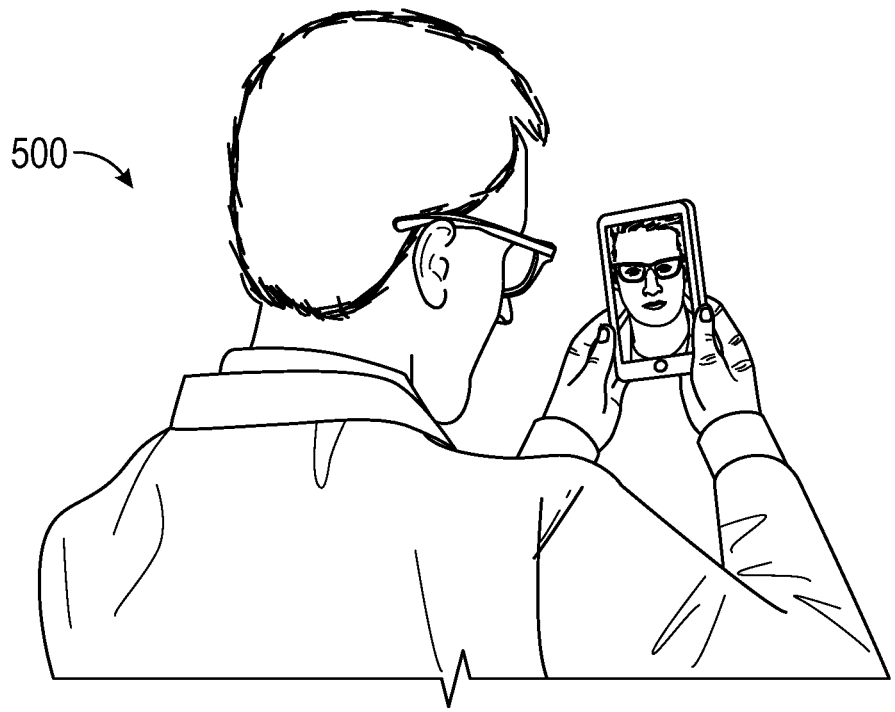

Description of a Disclosed Method and System of Calibration Frame Based PD Measurement a) A user may employ a personal electronic device or smart phone and a calibration frame, with the calibration frame sometimes being sometimes devoid of lenses.

b) As shown in FIG. 2 a user may wear disclosed calibration frame set and take a self-picture or selfie, with the captured imaged used for processing as described herein.

c) The captured image is processed using image recognition to detect the pupils and the calibration marks ("Ts") of the calibration frames.

d) The plane of the frames may be parallel to the plane of the pupils of the user.

e) The system captures the location of the calibration marks and the center points of the pupils and generates a 2D map of the relative pixel distances of the located objects.

f) By use of the geometry of the calibration frames and eyes, the 2D image is mapped to the 3D location of the calibration frame marks and the pupils of the eye.

g) After obtaining the pixel location on the captured image, transforming the data, toward finding PD measurements, may require:

1. knowledge of the camera field of view—for example an iphone 6 has a field of view 73 degrees.

2. Knowledge of the camera screen dimension w, and h and pixel density.

3. Knowledge of the location of the camera on the phone compared to the center of the phone 4. knowledge of the absolute vector distances between the 3 frame calibration marks, the "T"s such as 260, 263 and 265.

5. knowledge of the distance between the frame plane and the parallel pupil plane, which is estimated to be about 12 mm 6. determining the orientation of the frame plane from the cameras image plane. The default position is for the frame plane to be along the image plane of the camera.

7. The distance to the camera to the calibration marks is made knowing the field of view of the camera, and the number of pixels between the calibration marks 8. From that an estimate of the distance of the eye to the camera is made and from that an estimate of the vergence is made.

9. to the is estimated and from that is estimate is made of the vergence of the eye 10. Using this 3D geometry the calculation gives the (1) Distance PD (2) Near PD (3) L-PD and R-PD, referred to as dual PD 11. As a check the calculated PD is equal to the sum of the L-PD and R-PD. These values are calculated independently so it serves as a check 12. The data is displayed and then the user has the option to manually adjust the overlap of the lines with the Reference Frame marks or "Ts", little T's and the center of the Pupils, shown as + signs or calibration cross hairs 300.

13. When the user is satisfied they hit the check mark 710 or other screen generated 710 and the PD is displayed. The PD can also be uploaded and tracked.

Figure 3:
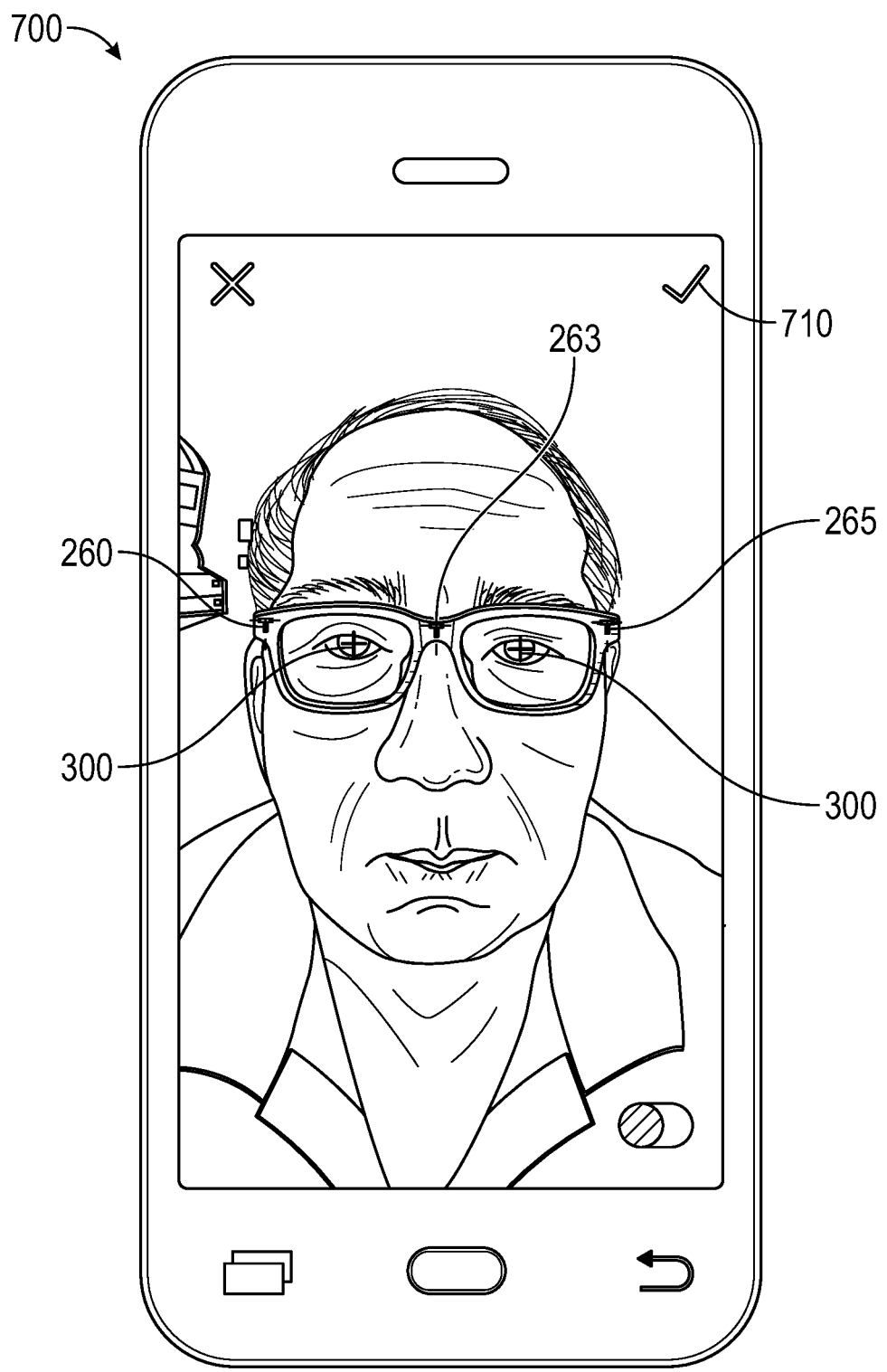

Referring to FIG. 3, five markers, comprising three "T"s 260, 263 and 265 and two center points or cross hairs 300 for pupils are shown, with a system employing auto image detection. An exploded view of a "T" marker is presented in the upper left hand side of FIG. 4.

Figure 5:
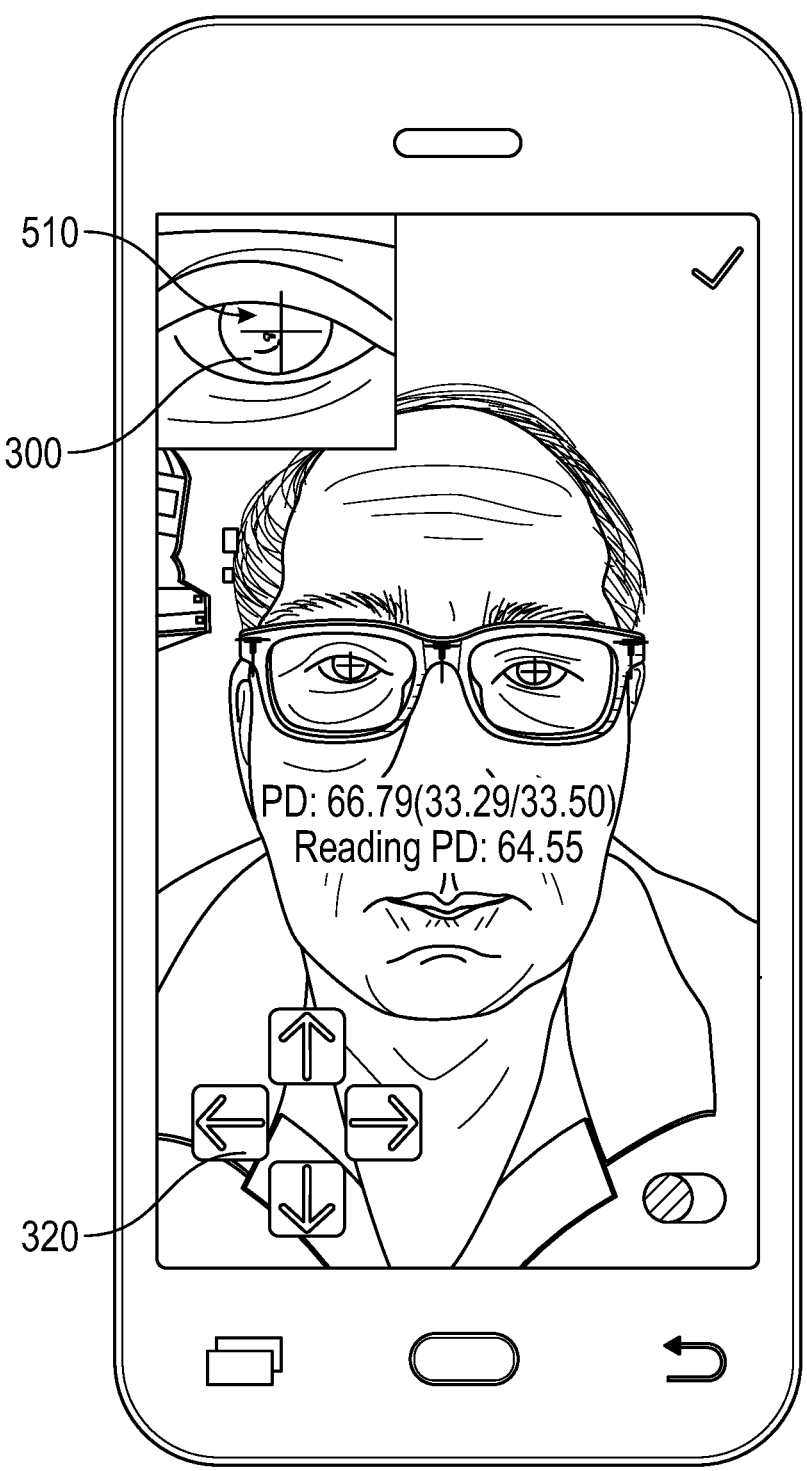

Referring to FIG. 5, manual adjustment means 320 are shown and an exploded view of a pupil 510 and pupil marker 300 are shown in the upper left hand side. The manual adjustments 320 and related interfaces are sometimes called a "tweak adjustments."

Figure 6:
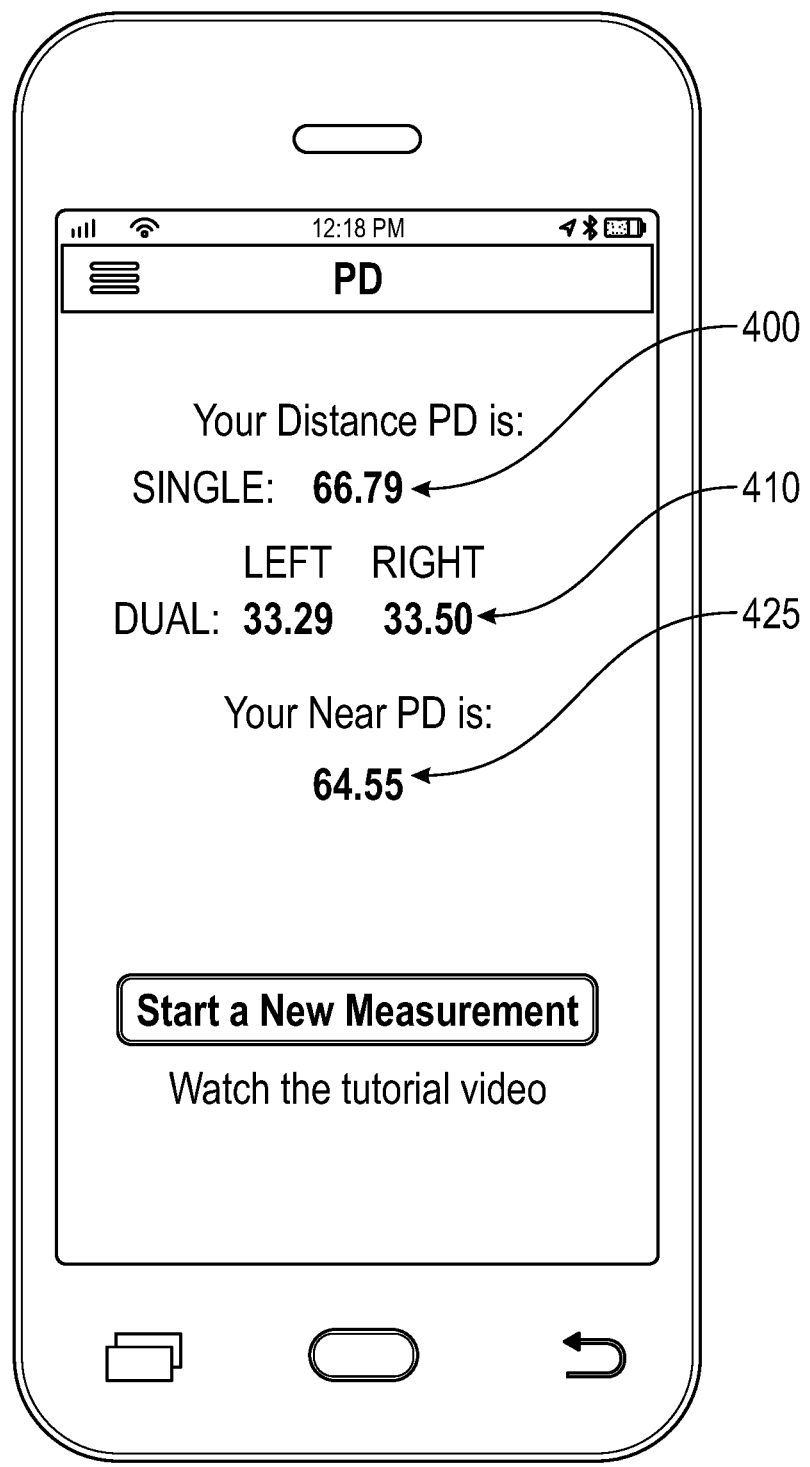

FIG. 6 depicts an output interface showing single PD values 400 and dual PD values 410 and a near PD value 425.

Figure 7:
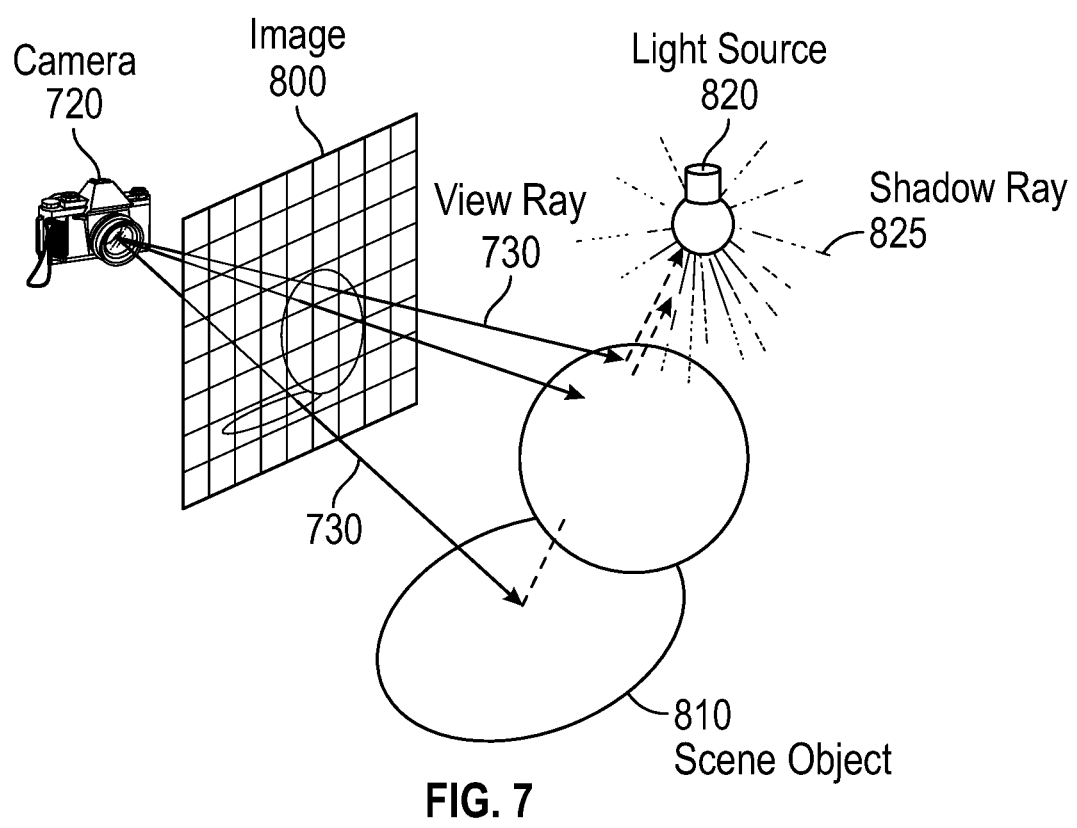

FIG. 7 depicts a camera and ray structure, sometimes used for ray tracing and distance measurement, sometimes used to measure distance between an object and the camera or lens of the camera. In a disclosed embodiment, a smartphone camera is treated as an observer located at the origin point of a 3-dimensional space. A real-world object point can emit a ray hitting the camera's sensor unit, which becomes a pixel point in the image. The image resides on a 2D plane comprised of pixels.

An important parameter for subsequent calculations is the camera's field-of-view. The field of view differs with different cameras, but the phone configuration generally provides the needed camera information.

Figure 8:
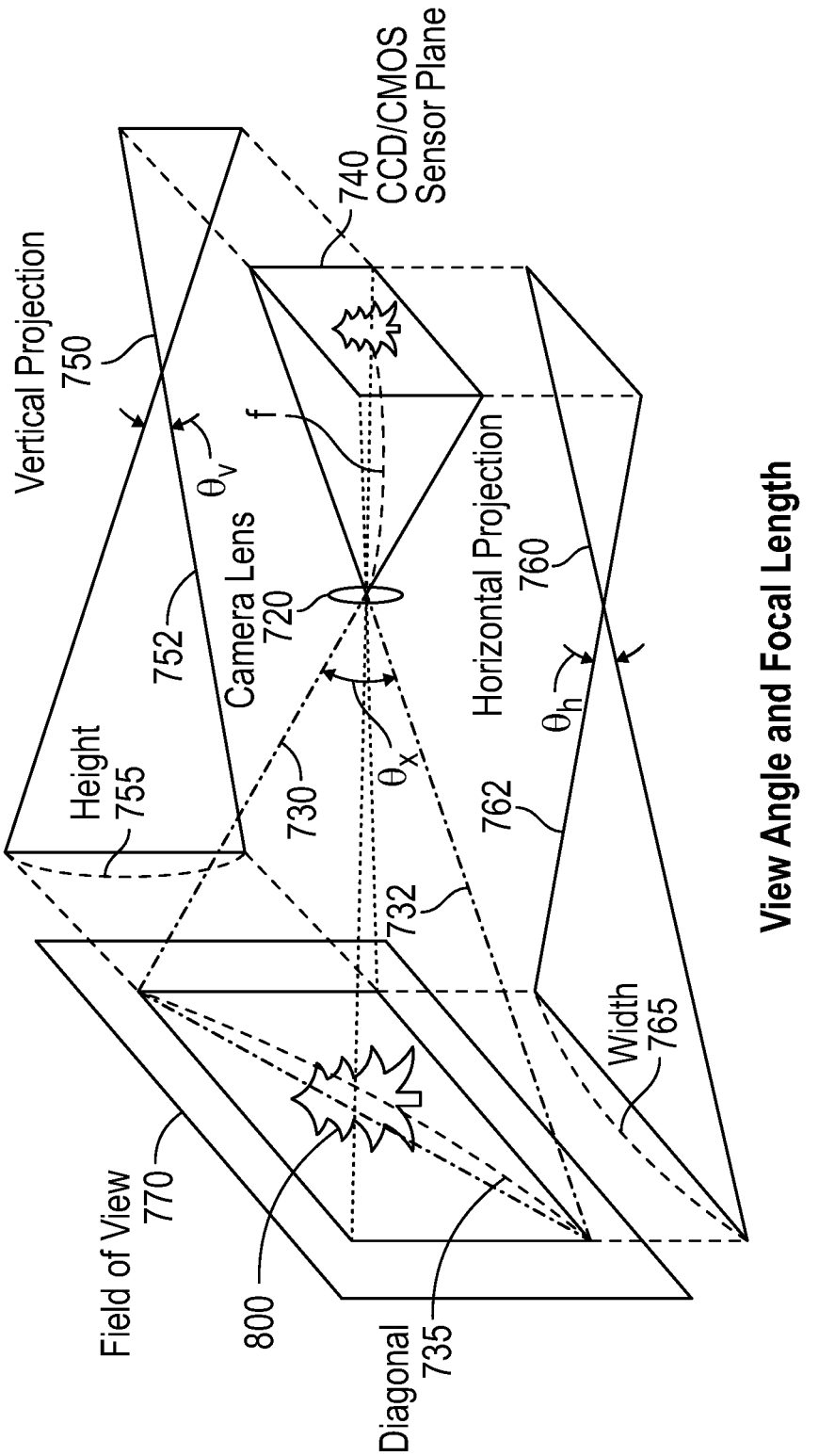

FIG. 8 depicts a field of view and related projections. While physically, the camera's sensor is located behind its lenses where the image is projected on the CCD sensor plane, disclosed embodiments may use the virtual image plane in front for calculations and mapping from 2D space to 3D locations. FIG. 8 depicts a lens 720, a sensor plane 740 and a field of view 770 and image 800. Vertical projection lines 750, horizontal projection lines 760 and diagonal projection lines 730. The projection lines may have a point of origin at the lens 720 and may project to both the forward filed of view and reward sensor plant 740. The angles 732, 752 and 762 of the projection lines along with the distances between the camera lens and field of view and between the camera lens and sensor plane may be used to ascertain distances of objects or features found in the filed of view 770 or image 800.

Figure 9:
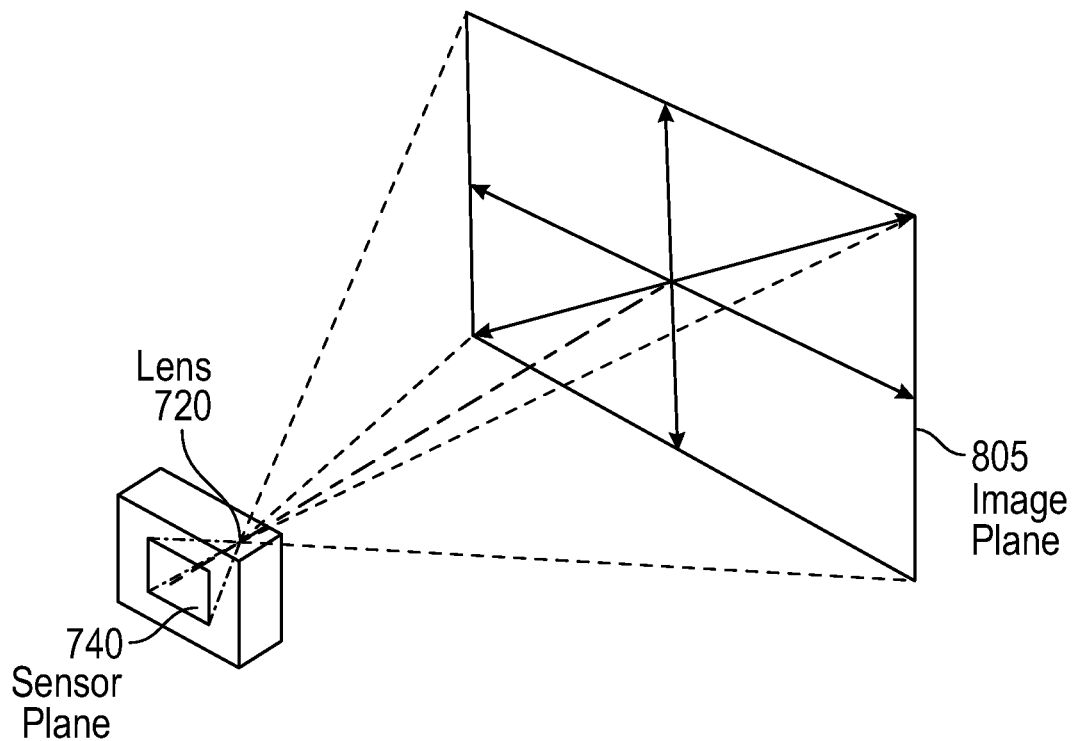

FIG. 9 depicts a virtual image plane 805 as well as a lens 720 and sensor plane 740.

Figure 10:
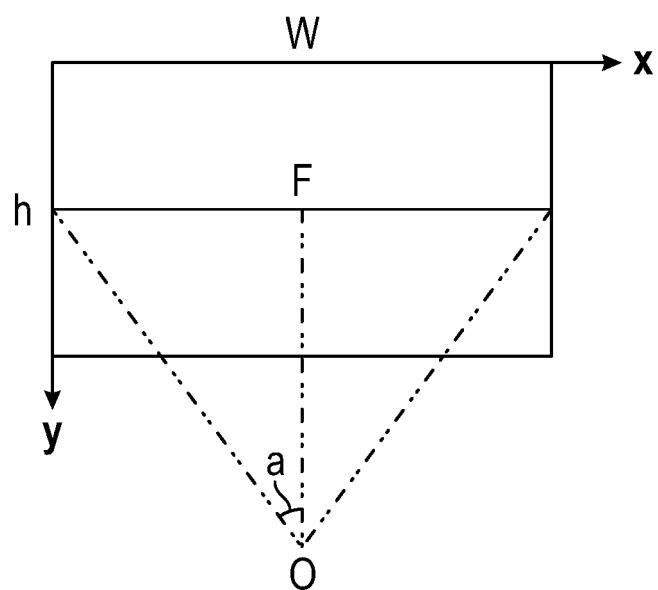

Referring to FIG. 10, the maximum field of view angle from the smart phone operating system, in given in degrees and also discloses the image dimensions from the image loader, in pixels. Then, the distance between the virtual image plane and the camera can be calculated by using the equation below:

$$f=(w/2)/\tan(a/2)$$

For a phone with a field of view of 76 degrees, and the maximum dimension of the display is 5" or 2000 pixels, with a 400 ppi pixel density, f=1200 pixels.

FIG. 10 depicts a pixel coordinate system, which may be comprised on w x pixels and h y pixels. In other words width may be known as "w" and measured along the x axis and height may be known as "h" and measured along the y axis. The center of the image is designated and the camera is oriented on the axis perpendicular to the plane and passing through the center point, (w/2, h/2).

Where "f" is the image distance OF (virtual focal length), in pixels. "w" is the maximum width of the image. "h" is the maximum height of the image. "a" is the maximum field of view angle. Assume that the camera is focusing on the center point of the plain, where the pixel coordinate system (0,0) is in the upper left corner of $$F=(w/2,h/2,f)$$

Then, for each pixel on the image with 2D coordinates (start from the top left corner) P(px, py), its is $$P=(p_x-w/2,p_y-h/2,f)$$

with respect to the camera.

Let the target object (T) be located somewhere far away well past the pixel imaging plane. Let $\vec{r}$ be the normalized vector of $\overrightarrow{OP}$.

$$\vec{r} = \left( \frac{p_x - \frac{w}{2}}{\sqrt{\left(p_x - \frac{w}{2}\right)^2 + \left(p_y - \frac{h}{2}\right)^2 + f^2}}, \frac{p_y - \frac{h}{2}}{\sqrt{\left(p_x - \frac{w}{2}\right)^2 + \left(p_y - \frac{h}{2}\right)^2 + f^2}}, \frac{f}{\sqrt{\left(p_x - \frac{w}{2}\right)^2 + \left(p_y - \frac{h}{2}\right)^2 + f^2}} \right)$$

"r" is the length of the ray. As long as we get the length of the ray, we can calculate the target coordinates (T):

$$T = O + r * \vec{r} = r * \vec{r}$$

We now have the relation between the direction of the Target Object and it location on the 2D pixel plane.

Figure 11:
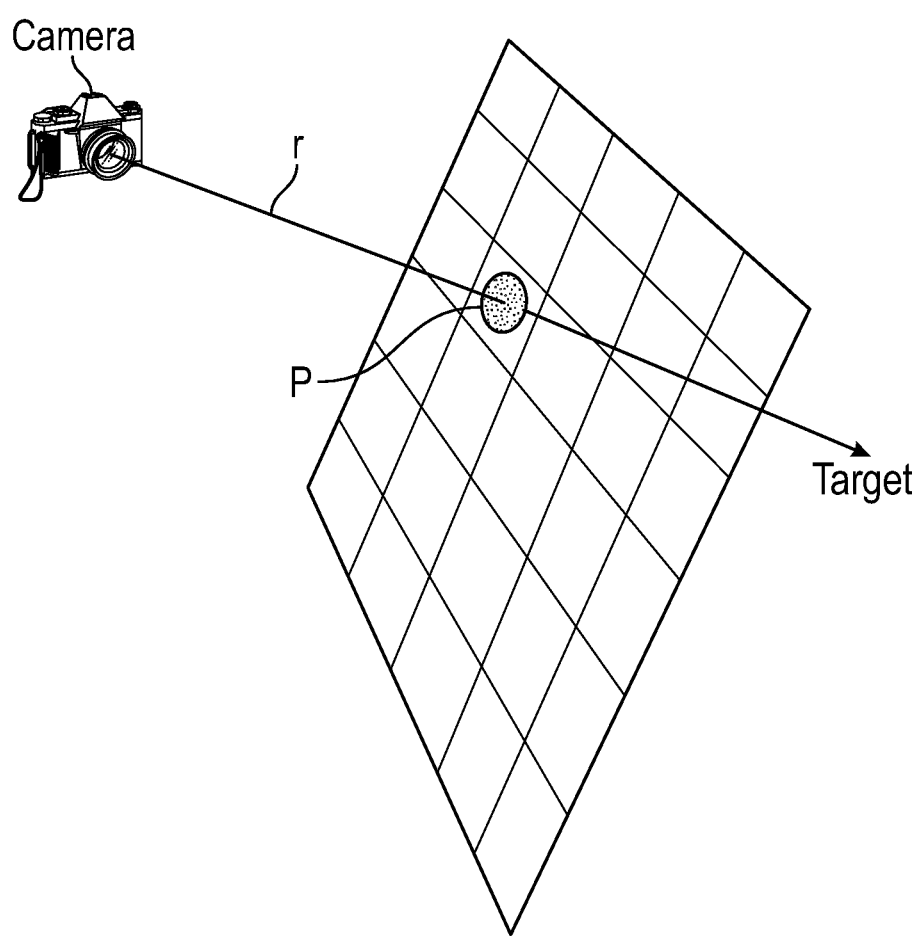

FIG. 11 depicts a location of a target object beyond the imaging plane, with vector "r" parallel to the target.

Figure 12:
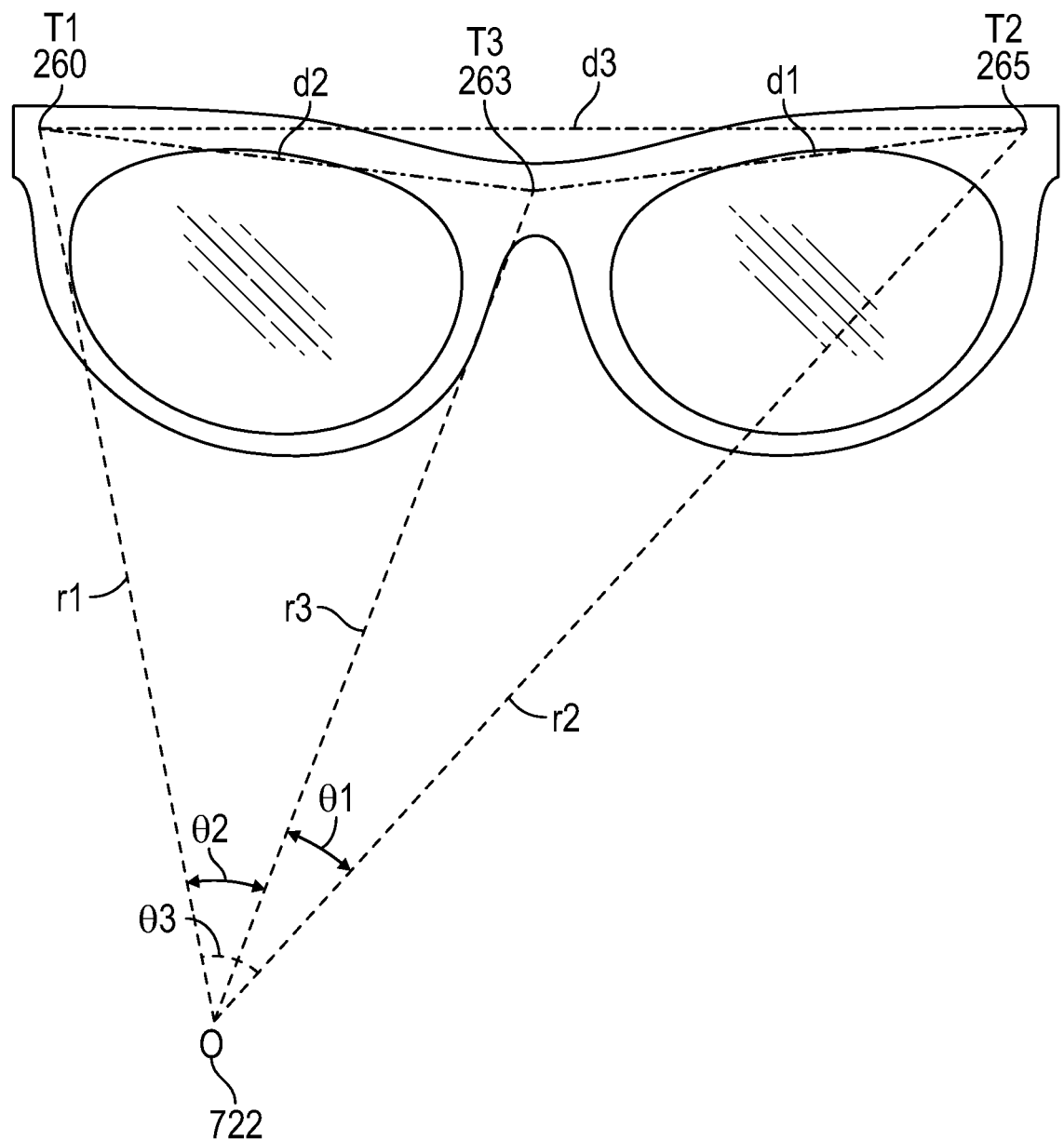

FIG. 12 depicts geometry of a disclosed calibration frame. In some disclosed embodiments, a calibration frame may comprise three "T" markers 260, 263 and 265 on the surface of the outer side of the frame. FIG. 12 further depicts calibration frames with engineered and known dimensions, d1, d2, d3 and angles showing the relation between T1, T2, T3 the calibration points.

Let $T_{1\ 260}$, $T_2$ 265 and $T_3$ 263 be the 3 markers. We know the distance between each of them from the design of the frame $$d2=|T_1T_3|=64.5/\cos(9°)=65.304 \text{ mm}$$

$$d1=|T_3T_2|=64.5/\cos(9°)=65.304 \text{ mm}$$

$$d3=|T_2T_1|=64.5+64.5=129 \text{ mm}$$

let $\vec{r_i}$ be the normalized vector of each ray, and $r_i$ be the length of the ray. We shoot 3 rays to the markers:

$$T_1 = \overrightarrow{OT_1} = \vec{r_1} * r_1$$

$$T_2 = \overrightarrow{OT_2} = \vec{r_2} * r_2$$

$$T_3 = \overrightarrow{OT_3} = \vec{r_3} * r_3$$

We can calculate those normalized vectors by using their pixels location on the image plane.

We can also calculate the angles between each ray by using the dot product law:

$$a \cdot b = |a| \times |b| \times \cos(\theta)$$

Then we get:

$$\theta_3 = \arccos\left( \frac{\vec{r_1} \cdot \vec{r_2}}{|r_1| * |r_2|} \right)$$

-continued $$\theta_2 = \arccos\left(\frac{\vec{r_1} \cdot \vec{r_3}}{|r_3| * |r_3|}\right)$$

$$\theta_1 = \arccos\left(\frac{\vec{r_3} \cdot \vec{r_2}}{|r_3| * |r_2|}\right)$$

For triangle $OT_1T_2$, $OT_2T_3$ and $OT_1T_3$, we can get 3 equations by using the law of cosines:

$$r_1^2 + r_2^2 - d_3^2 - 2r_1r_2\cos(\theta_3) = 0$$

$$r_2^2 + r_3^2 - d_1^2 - 2r_2r_3\cos(\theta_1) = 0$$

$$r_1^2 + r_3^2 - d_2^2 - 2r_1r_3\cos(\theta_2) = 0$$

We can solve the ternary quadratic equations above and get $r_1$, $r_2$, $r_3$. There will be 4 sets of real solutions. We can easily filter out the 2 negative results. Also, we know that the center "T" mark is closer to the camera because the user wearing it is facing to the camera. So, we can add conditions below to get the only correct solution:

$$T_3 \cdot z < (T_1 \cdot z + T_2 \cdot z)/2$$

$$r_1 > 0$$

$$r_2 > 0$$

$$r_3 > 0$$

In the simple case where the center T is at the center virtual display and the calibration frames front plane is parallel then the equation simplifies greatly to $$r = d_3/(\sqrt{2}(1 - \cos(\theta_3)))$$

Figure 13:
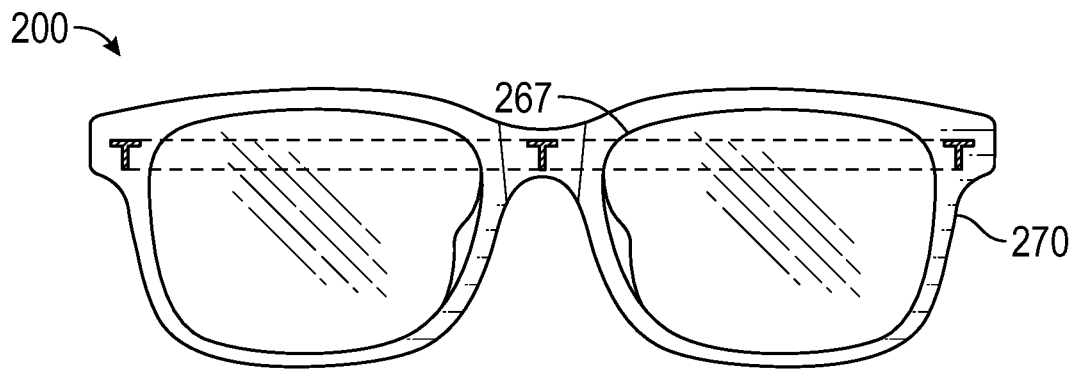
Figure 14:
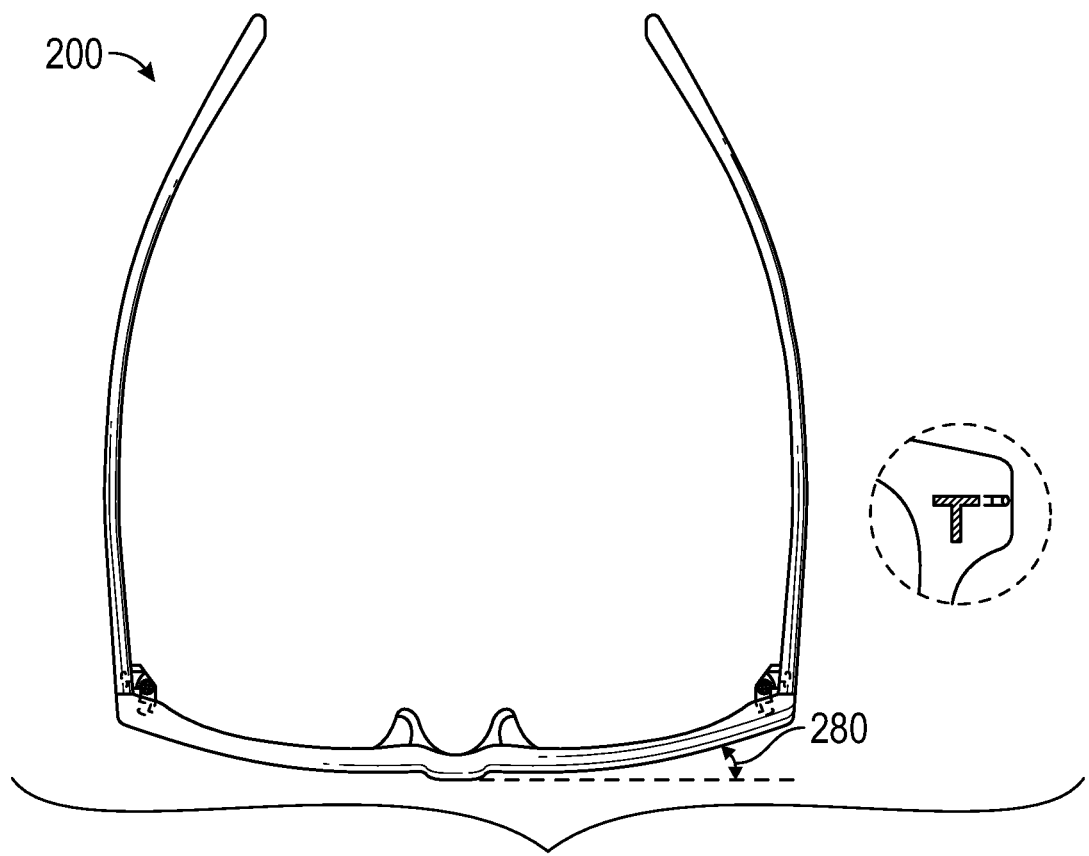
Figure 15:
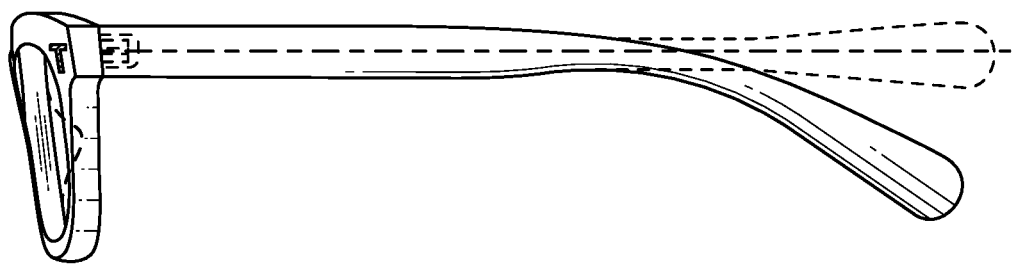

FIGS. 13, 14 and 15 depicts a disclosed calibration frame 200 sometimes being white in color and being devoid of lenses. A calibration frame may comprise three "T" markers printed or disposed upon the frame surface 270. All three "T"s may reside upon the same horizontal plane 267 as shown in FIG. 13. The center T 263, however; may protrude a by a relatively small distance, as shown in FIG. 15. corresponding to the 9 degree angle 280 shown in FIG. 15.

A disclosed PD measurement system may include a smartphone program that allows users to measure their PD, by wearing a disclosed calibration frame 200 and taking a picture of themselves. The app loads the camera parameters and calculates the image distance based on the pixel resolution and field of view. Then, the app does image processing for pattern recognition of the calibration T and pupils of the eye.

A first step may be to recognize the user's face and eyes inside the face. In this example both use the Haar Cascades method provided by the OpenCV library.

Frame Detection and "T" Markers Recognition

The face recognition and eye detection result is used as a reference for the PD frame recognition. The location of the PD frame on the image should be somewhere above the nose, below the hair and between the ears. We can create such a bounding box to remove background noise and speed up searching. If the frame is not detected the app gives an error message that the frame has not been found.

The surface color of a disclosed calibration frame is pure white. By changing the contrast value, we can easily remove gradient information within the frame body. However, human face has its own gradient features regardless of the skin color. As result, canny edge detection becomes a good solution to find the frame edges. By searching for pixels with largest gap in gradient value, we can find the frame edge. An example can be found in FIG. 16.

Figure 16:
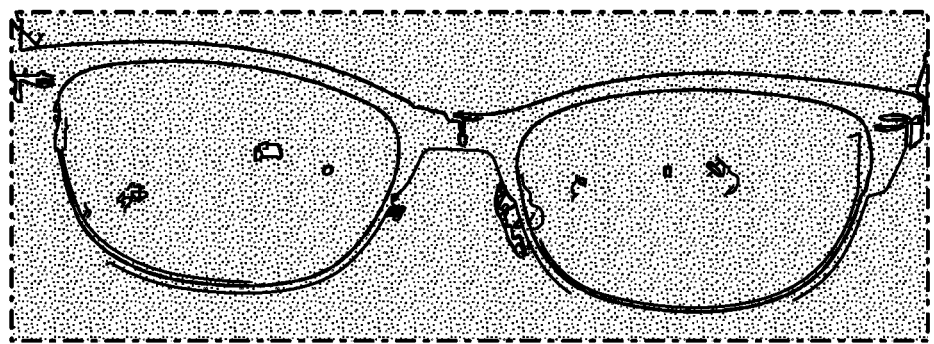
Figure 17:
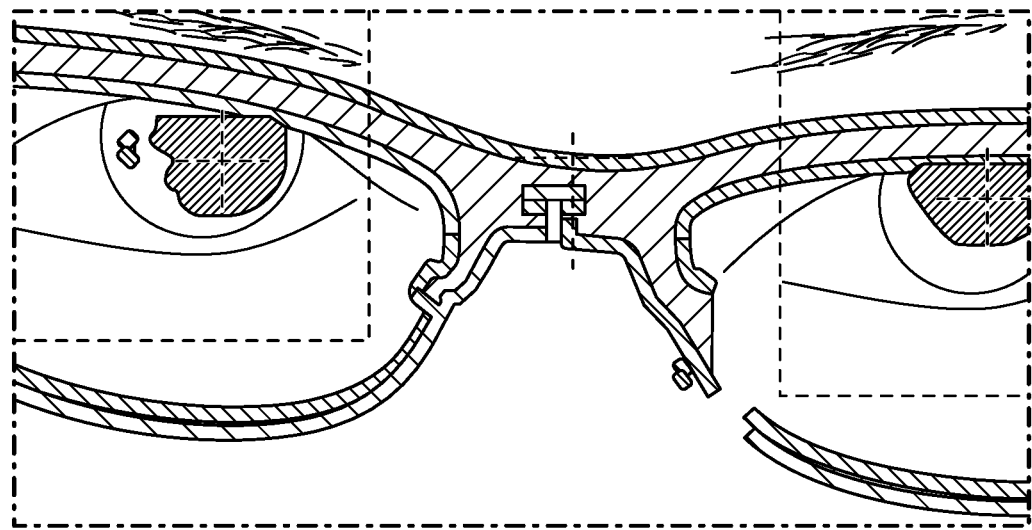

The result of Canny edge detection contains lots of noise. The next step is to find the frame upper edge and lower edge. This can be done by looking for white pixels between those Canny edges, as shown in FIG. 16. The information of upper edges(red), lower edges(blue) and frame body pixels(yellow) can be extracted from the image, as shown in FIG. 17.

Figure 18:
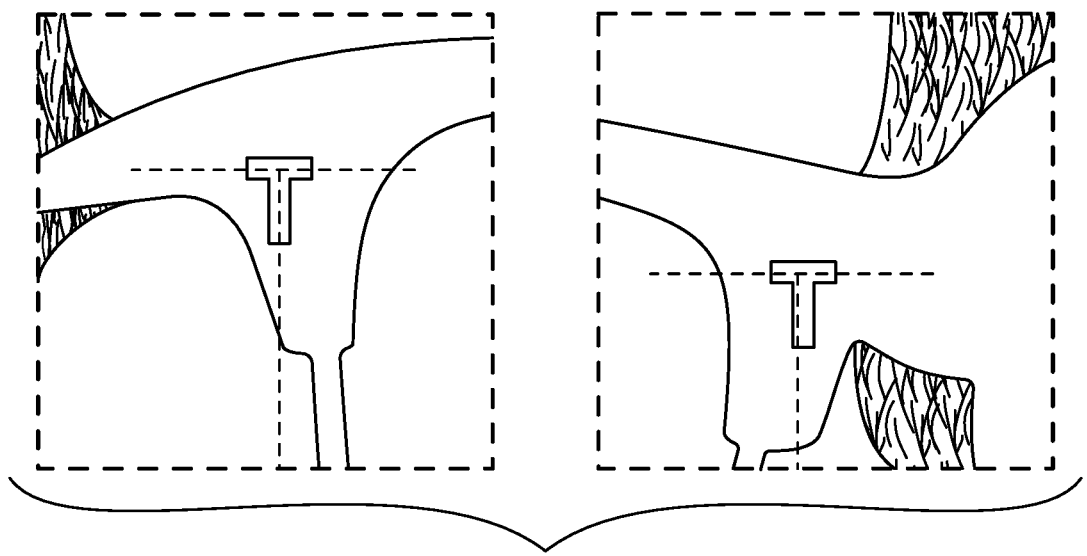

Referring to FIG. 18, the "T" markers are in pure black. The middle "T" marker will generate a horizontal gap at the center of the frame body. By measuring the width and height of the gap, we can extract those pixels surrounding the "T" marker. As long as we find the middle "T", we can generate a template for the template matching algorithm, because we know that there are two more exactly same markers on the frame. The template matching result is shown in FIG. 18. The pixel coordinates of the "T" markers are then used to calculate the real-world coordinates.

In regards to pupil detection, we assume that the plane of user eyes is about 18 mm away behind the middle "T" marker. This value is chosen based on measurements and experiments. In order to get the real-world coordinates of the pupil center, we have to find them on the image. The Haar Cascades result give the bounding box of the eyes, but not pupils. Image segmentation and clustering method is used to find the pupil, like DBSCAN and k-means clustering.

The automatic recognition result can be tweaked through manual intervention. The measurement app gives user flexibility to adjust the markers for accurate result. There are 5 markers to be refined: the left "T" marker, the middle "T" marker, the right "T" marker, the left pupil marker and the right pupil marker. After such a manual adjustment, we can calculate user's PD information based on their pixel location on the image.

Figure 19:
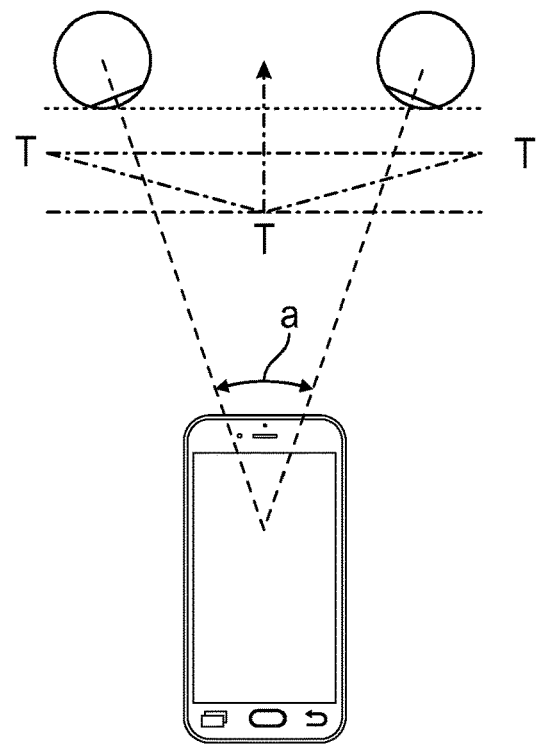

Once we find the pixel position of the pupils, and the markets we can easily calculate the normalized vector from the camera to the pupils. In 3D space, a plane can be determined either by a triangle on it, or by a point on it with the plane vector normalized. The position of 3 "T" markers can determine the horizontal plain of the frame. We know that the frame is symmetric, so we can use the middle vector of the frame and the middle "T" marker to find the vertical plane. We assume that the middle "T" is 18 mm away from the center of the pupils, which is on the pupil plane using the same plane vector because they are parallel to each other. An example may be found in FIG. 19. which shows a relation between the eyes to the calibrations frames.

Once we found the pupil plane,

We first calculate the current single PD based on marker positions, which is the distance between the centers of the left and right pupil.

$$\text{current\_pd} = \sqrt{(x_{left} - x_{right})^2 + (y_{left} - y_{right})^2 + (z_{left} - z_{right})^2}$$

Figure 20:
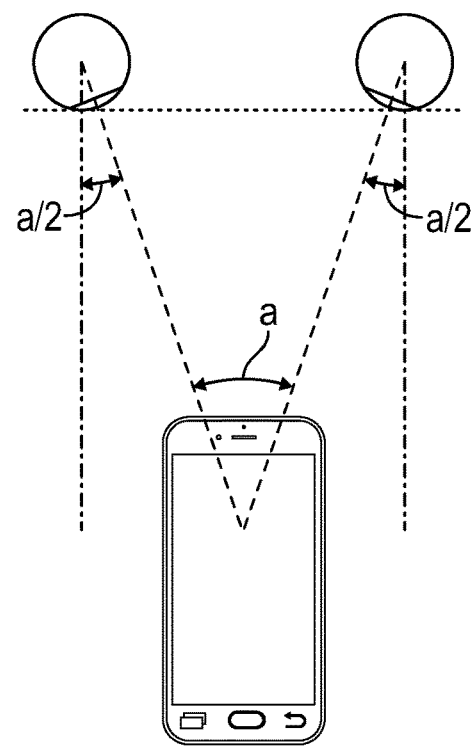

We know that user is looking at the phone in a close distance which is at a close distance. Therefore this does not represent the distance PD. However, distance PD is more useful when user wants to purchase glasses. We can add such a distance PD correction on each side. There is another small error caused by the distance between the intersection point of the pupil plane and the real pupil center. The error can be seen or is represented in FIG. 20.

As a result, the total distance PD correction=2*$r_e$*tan(a/2) Where $r_e$ is the human eyeball radius. 90% of the Human population have the same eyeball radius which is 12 mm+/− 0.5 mm.

This correction is added to the current PD to give the Distance PD.

Figure 21:
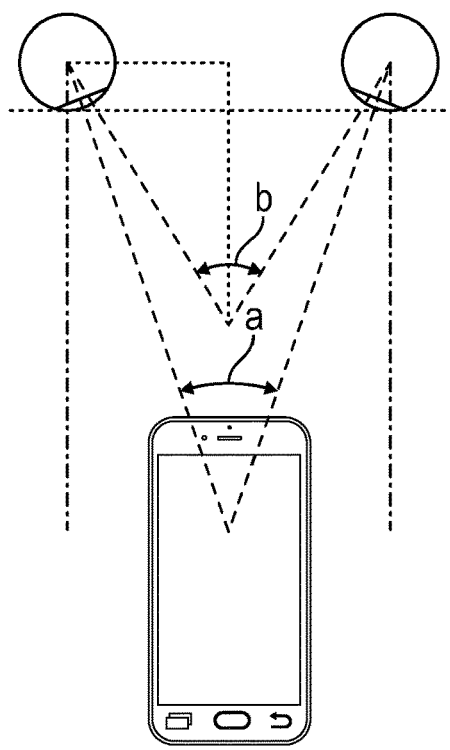

Referring to FIG. 21, measurement of the near PD is quite useful for reading glasses or progressive glasses. The normal reading distance is about 14 inches, which is 355.6 mm.

So, we can calculate the near PD based on the distance PD.

near_pd=distance_pd−2.0*tan(*b*/2)

Where b is the angle between the 2 rays from user eyes to the reading point.

*b*=2*arctan((distance_pd/2.0)/(reading_distance+eyeball_radius))

Usually the near PD is 2~3 mm smaller than the distance PD.

Figure 22:
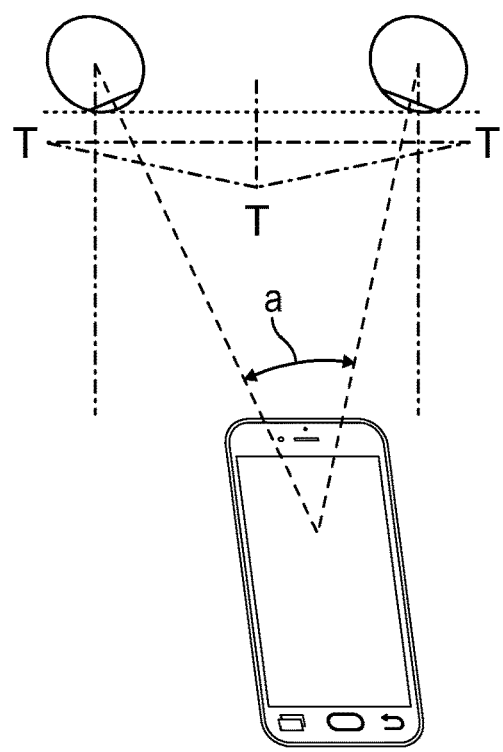

Referring to FIG. 22, the challenge of calculating dual PD is addressed. Some people have different pupillary distance for each eye. To calculate the dual PD, we have to measure the distance between the eyeball center to the nose center, the nose bridge (close to the middle "T" marker). The eyeball center is just 12 mm away from the pupil. So, we can find them by moving the pupil intersection points backward along the direction of their vector of the rays.

Figure 23:
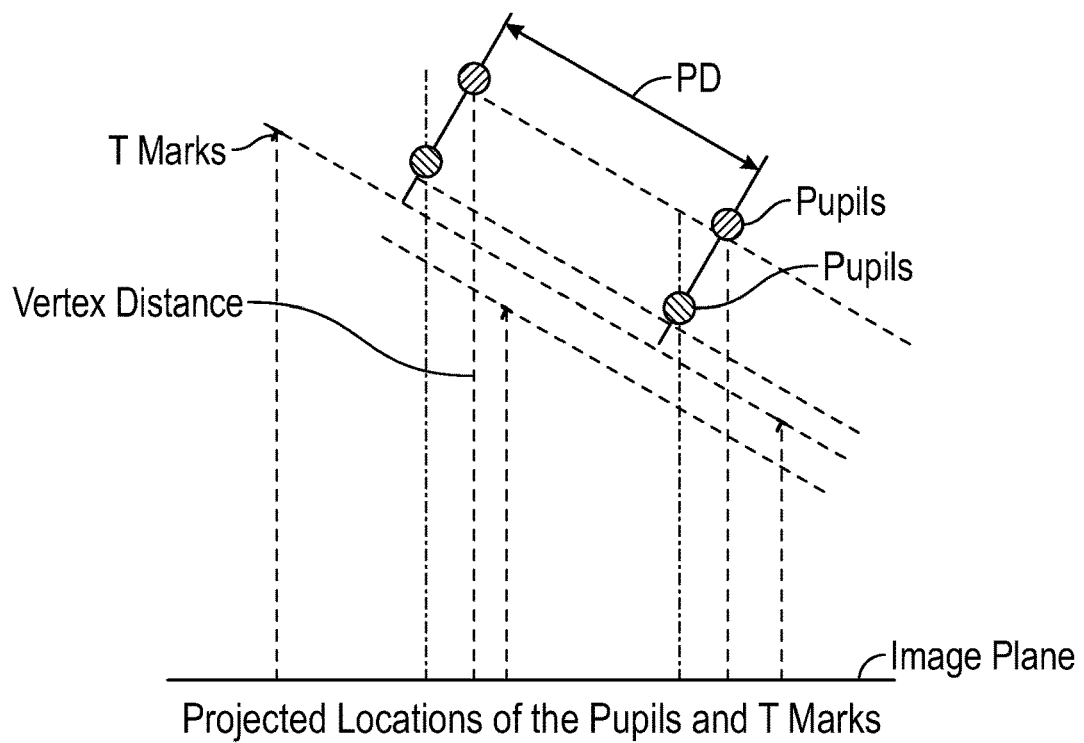
Figure 24:
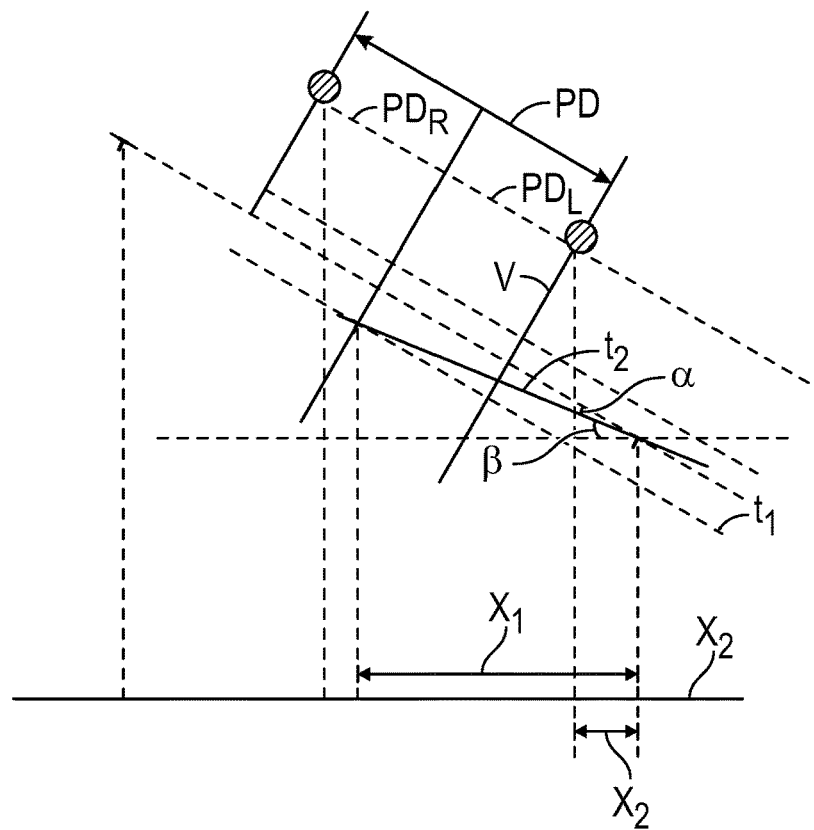

In another embodiment of the invention, a method to measure a person's vertex is proposed by taking two images at different angles. The images could then be used to calculate the vertex of a person. FIG. 23 shows the expected difference between two different vertex values. The images are a 2D projection of the 3D reality and thus have different representations for the different vertexes. FIG. 24 shows a schematic representation of the geometry. The methodology presented in previous embodiments could be used as a form of calibration of the image from pixels to real world measures. The following geometrical calculation is an example of a calculation that could be used to find the vertex:

$$V = \frac{t_1}{2} + \left[t_2\cos(\alpha) - PD_L - \frac{x_2}{\cos(\alpha + \beta)}\right]\cot(\alpha + \beta)$$

Figure 25:
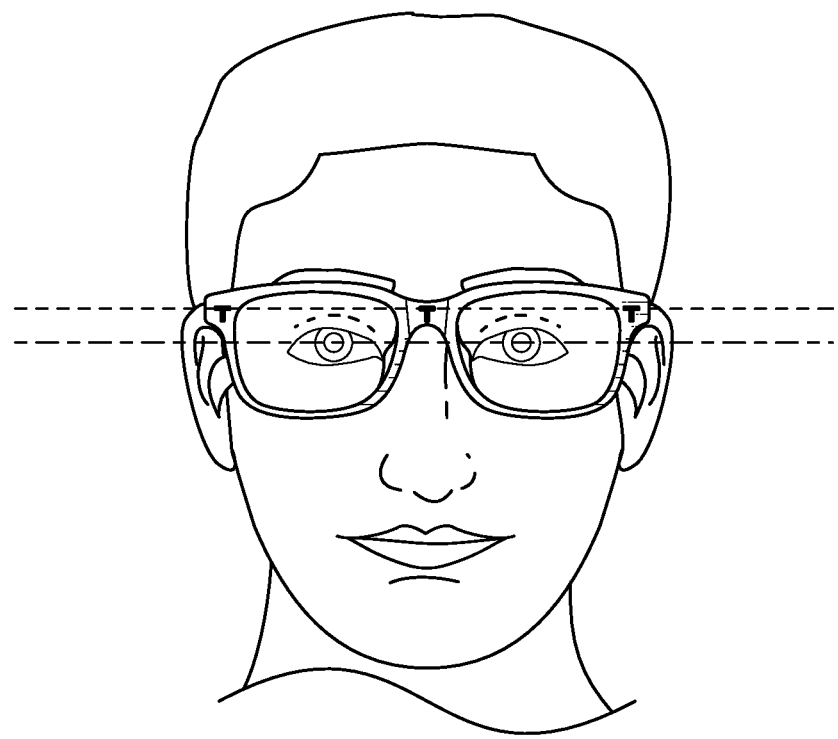

In another embodiment of the invention, two images could be used to calculate the centerline of the pupil. The angle should be taken in the vertical axis (up-down) and similar calculations could be used to find the location of the pupil with relation to the Ts in the vertical direction in space. FIG. 25 presents a proposed implementation of the embodiment. The center line is especially important for bifocal, tri focal and progressive glasses. Similar calculation as proposed in previous sections could be implemented to account for gaze direction when taking an image in a selfie mode from an angle. This could be implemented for any of the calculations above (vertex or centerline). As the camera angle is inferred from the image, the calculation can take the into account an assumption that the user is looking into the camera. Special attention should be taken for gaze direction limit of human eyes.

Figure 26:
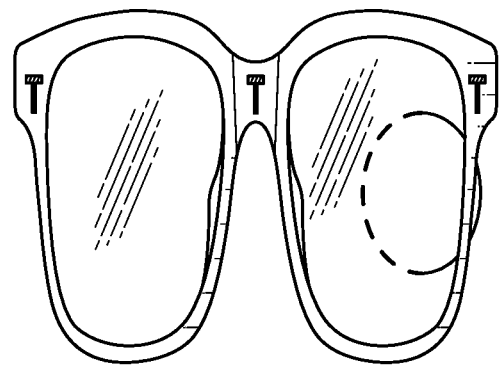

In yet another embodiment of the invention, a close-up image could be taken from and angle and a curve could be fit to the cornea curvature imaged. That curve could then be used to find the base curve of the cornea for matching of contact lenses. FIG. 26 presents a proposed implementation. In an example implementation the frames could be adjusted to have more marks on their side (FIG. 15). This will allow for more reference points for easier calculations when taking images from oblique angles or of a profile. This will allow for a more straightforward calculation of the cornea curvature and enable simpler determination of the base curve.

The use of a "T" as markings upon the frames is of benefit in allowing a lens and/or related system, such as a smart phone to locate the predefined reference points such as reference points 260, 263 and 265.

Further Embodiments and Features:

The use of specially designed calibration eyeglass frames in conjunction with a smart phone app/camera and a 3D geometric model to create a simple, convenient, natural and accurate method to measure PD.

Once the PD is known, it is possible to get accurate measure of the dimensions of a person's face.

Once the PD is known it is also possible to place virtual eye glass frames on the user image to see how they fit and to determine where the optical center needs to be with respect to the frames.

With this method one can easily determine various values of PD for near values as well as far values.

What is claimed is:

1. A system for measuring pupillary distances (PD) using eyeglass frames (200), with the eyeglass frames comprising reference indicia, the system comprising:
   a) the reference indicia of the eyeglass frames comprising a first marking (260) disposed upon a right temple area of the eyeglass frames, a second marking (265) disposed upon a left temple area of the eyeglass frames and a third marking (263) disposed upon a center area of the eyeglass frames;
   b) a lens (720) to find angles from the lens to the first, second and third markings;
   c) the positions of the first, second and third markings of the eyeglass frames to determine a horizontal plane of the third marking of the eyeglass frames to determine a vertical plane, these two planes are considered the pupil plane wherein a current single PD is derived by using the x and y axis of a left and a right pupil as derived from marker positions (300), the marker positions derived from a personal electronic device, wherein $$\text{current\_pd} = \sqrt{(x_{left} - x_{right})^2 + (y_{left} - y_{right})^2 + (z_{left} - z_{right})^2}.$$

2. The system of claim 1, wherein the first, second and third markings are within a surface (267) of the eyeglass frames.

3. The system of claim 2, wherein the third marking is disposed outwardly as compared to the first and second markings.

4. The system of claim 3, wherein the third marking is in the range of 5 to 12 degrees forward from the first and second markings.

5. The system of claim 1, wherein the first, second and third markings are in the form of a "T".

6. The system of claim 1, further including the lens (720) to find angles from the first, second and third markings and the pupils of a user and using said angles to derive a pupillary distance of the user.

7. The system of claim 6, further including a personal electronic device to derive said angles of claim 6.

8. The system of claim 6, further including a camera to derive said angles of claim 6.

9. The system of claim 1, wherein a correction is added to the current PD to find a distance PD, the correction being $2*r_e*\tan(a/2)$, wherein $r_e$ is a human eyeball radius and $(a/2)$ is the an angle from a camera lens to the user's pupils.

10. A method of measuring pupillary distances (PD) using eyeglass frames (200), with the eyeglass frames comprising reference indicia, the method comprising:
  a) providing the reference indicia of the eyeglass frames comprising a first marking (260) disposed upon a right temple area of the eyeglass frames, a second marking (265) disposed upon a left temple area of the eyeglass frames and a third marking (263) disposed upon a center area of the eyeglass frames;
  b) finding angles from a lens (720) to the first, second and third markings, by the lens;
  c) finding angles from the first, second and third markings and the pupils of a user, by a lens, and using said angles to derive a pupillary distance of the user;
  d) determining a horizontal plane of the third marking of the eyeglass frames, to determine a vertical plane, using the position of the first, second and third markings of the eyeglass frames, these two planes are considered the pupil plane wherein a current single PD is derived by using the x and y axis of a left and right pupil as derived from marker positions (300), the marker positions derived from a personal electronic device, wherein $$\text{current\_pd} = \sqrt{(x_{left} - x_{right})^2 + (y_{left} - y_{right})^2 + (z_{left} - z_{right})^2}.$$

11. The method of claim 10, wherein the first, second and third markings are within a surface (267) of the eyeglass frames.

12. The method of claim 10, wherein the third marking is disposed outwardly as compared to the first and second markings.

13. The method of claim 12, wherein the third marking is in the range of 5 to 12 degrees forward from the first and second markings.

14. The method of claim 10, providing an indicia of a "T" as the first, second and third markings.

15. The method of claim 10, including the step of adding a correction to the current PD to find a distance PD, the correction being $2*r_e*\tan(a/2)$, wherein $r_e$ is the human eyeball radius and $(a/2)$ is an angle from a camera lens to the user's pupils.

* * * * *